US009808646B2

(12) United States Patent
Piergallini et al.

(10) Patent No.: US 9,808,646 B2
(45) Date of Patent: Nov. 7, 2017

(54) DEVICE FOR PERSONAL USE IN PHOTOTHERAPY

(75) Inventors: Remigio Piergallini, Grottammare Ascoli Piceno (IT); Nikolaos Loupis, Athens (GR); Lise Hébert, Montreal (CA)

(73) Assignee: KLOX TECHNOLOGIES INC., Laval (CA)

( * ) Notice: Subject to any disclaimer, the term of this patent is extended or adjusted under 35 U.S.C. 154(b) by 287 days.

(21) Appl. No.: 12/913,747

(22) Filed: Oct. 27, 2010

(65) Prior Publication Data

US 2011/0123958 A1 May 26, 2011

Related U.S. Application Data

(60) Provisional application No. 61/255,300, filed on Oct. 27, 2009.

(51) Int. Cl.
| | | |
|---|---|---|
| *A61C 1/00* | (2006.01) | |
| *A61N 5/06* | (2006.01) | |
| *A61C 19/06* | (2006.01) | |
| *A46B 15/00* | (2006.01) | |

(52) U.S. Cl.
CPC .......... *A61N 5/062* (2013.01); *A46B 15/0034* (2013.01); *A61C 19/063* (2013.01); *A61N 5/0616* (2013.01); *A61N 2005/0644* (2013.01)

(58) Field of Classification Search
CPC ............................ A61C 19/004; A61C 19/066
USPC ........... 433/29–31, 80, 89, 215–216; 604/20, 604/290; 606/9; 607/88, 89, 90–93; 401/183–186, 264
See application file for complete search history.

(56) References Cited

U.S. PATENT DOCUMENTS

| | | | | |
|---|---|---|---|---|
| 2,853,728 A | * | 9/1958 | Nadai | 401/202 |
| 3,491,396 A | * | 1/1970 | Granieri, Jr. et al. | 15/104.94 |
| 5,017,036 A | * | 5/1991 | Vidovic | A45D 34/042 401/269 |
| 5,160,194 A | * | 11/1992 | Feldman | 362/109 |
| 5,566,823 A | * | 10/1996 | Summers | 206/209.1 |
| 5,737,792 A | * | 4/1998 | Quigless | 15/167.1 |
| 6,056,548 A | | 5/2000 | Neuberger et al. | |
| 6,623,272 B2 | * | 9/2003 | Clemans | 433/215 |
| 2003/0059738 A1 | | 3/2003 | Neuberger et al. | |
| 2004/0237226 A1 | | 12/2004 | Hohlbein et al. | |
| 2005/0026103 A1 | * | 2/2005 | Wasylucha | 433/29 |
| 2005/0053895 A1 | * | 3/2005 | Pinyayev et al. | 433/29 |

(Continued)

FOREIGN PATENT DOCUMENTS

| | | |
|---|---|---|
| DE | 3638696 | 5/1988 |
| DE | 19531368 | 2/1997 |

(Continued)

OTHER PUBLICATIONS

Extended European Search Report dated Mar. 3, 2013 for EP Application 10829599.9.

*Primary Examiner* — Yogesh Patel
(74) *Attorney, Agent, or Firm* — White & Case LLP

(57) ABSTRACT

There is provided an applicator cartridge for delivery of a photoactivatable composition to a treatment site, having an applicator head and a reservoir adapted to receive the composition, which may be used with a photodynamic therapy device comprising an illuminating member. Methods of using the applicator cartridge and the device are also provided.

26 Claims, 17 Drawing Sheets

(56) References Cited

U.S. PATENT DOCUMENTS

| | | |
|---|---|---|
| 2006/0047329 A1 | 3/2006 | Krespi et al. |
| 2008/0060148 A1 | 3/2008 | Pinyayev et al. |
| 2008/0176183 A1* | 7/2008 | Gatzemeyer et al. .......... 433/82 |
| 2008/0209650 A1 | 9/2008 | Brewer et al. |
| 2008/0255549 A1 | 10/2008 | Rose et al. |
| 2009/0056044 A1 | 3/2009 | Rizoiu et al. |
| 2009/0320224 A1* | 12/2009 | Hohlbein et al. ............ 15/167.1 |

FOREIGN PATENT DOCUMENTS

| | | |
|---|---|---|
| EP | 743029 A2 | 11/1996 |
| EP | 0872195 | 10/1998 |
| EP | 2263601 | 12/2010 |
| JP | 2002-142865 | 5/2002 |
| WO | WO9818364 * | 5/1998 |
| WO | WO-2006012752 | 2/2006 |
| WO | WO-2006/125204 A2 | 11/2006 |
| WO | WO-2007076405 | 7/2007 |

* cited by examiner

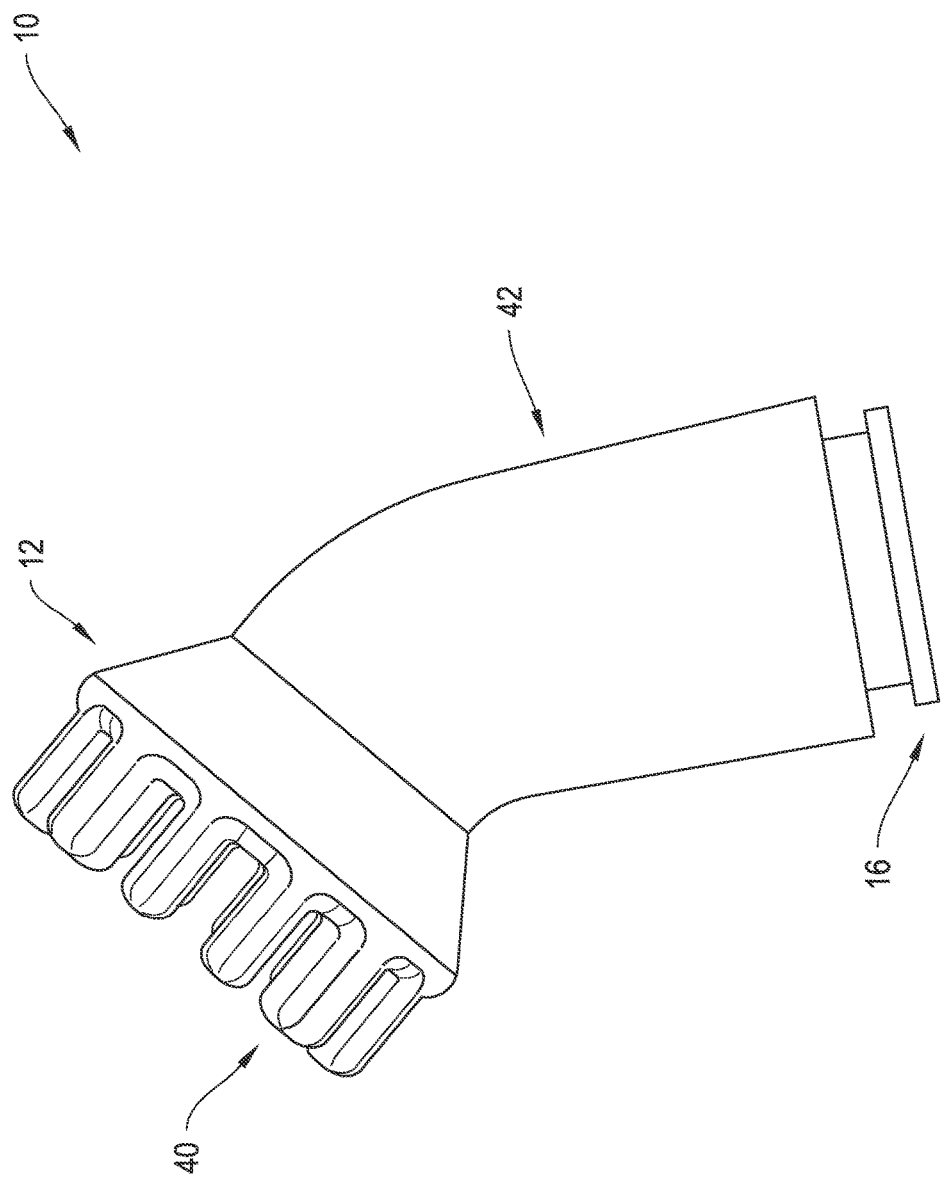

DEVICE FOR PERSONAL USE IN PHOTOTHERAPY

REFERENCE TO RELATED APPLICATIONS

This application claims the benefit of U.S. Provisional Application No. 61/255,300, filed Oct. 27, 2009, the disclosure of which is incorporated herein by reference in its entirety.

BACKGROUND (a) Field

The subject matter disclosed generally relates to a device for personal use in photodynamic therapy. More specifically, the subject matter disclosed generally relates to an applicator cartridge for delivery of a photoactivatable composition to a treatment site, which may be used with an illuminating member.

(b) Related Prior Art

Phototherapy has a wide range of applications to both the medical and cosmetic fields.

U.S. Pat. No. 6,056,548 to Neuberger et al. describes a method of destroying bacteria in the oral cavity, and promotes buccal hygiene using photoactive dyes and photodynamic therapy. This patent also describes using a bleaching agent, hydrogen peroxide, to photobleach and destroy the photoactive dye used for destroying bacteria. Photodynamic therapy of the skin using photoactive dyes such as Erythrosine B and/or Safranin O have been employed to destroy bacteria, as described in WO 05/032459 and WO 05/021094, both to Albrecht et al. The photoactive dyes are employed to directly destroy bacteria.

Phototherapy to perform non-ablative skin rejuvenation to repair, or offset, the results of both chronological- and photo-aging in the skin of the face, neck, hands and exposed areas of the body has become extremely popular. Clinicians have rapidly adopted the use of ablative skin rejuvenation using lasers, albeit with the negative effects of severe morbidity (erythema and oedema) resulting in patient downtime. These disadvantages significantly offset the good results of the treatment. Photorejuvenation techniques such as lasers and intense pulsed light (IPL) sources were then developed to deliver thermal damage to the dermis under cooling, termed non-ablative, skin rejuvenation. Laser ablative skin resurfacing has been a popular modality for the removal or improvement of major wrinkles and other severe symptoms of aging. The principles of ablative therapy are based on light-tissue interaction delivering the optimum amount of controlled residual thermal damage with precise epidermal ablation, therefore invoking a wound response and thus maximizing the clinical result while minimizing side effects and their associated downtime.

To date, photodynamic therapy has always been performed in a clinical setting. Trained professionals are needed to manipulate the substances and compositions used in the treatments, which may sometimes contain dangerous chemicals. Moreover, trained personnel are also required to operate the specialized equipment, such as laser lights, which may represent a hazard to the patient if improperly used. Additionally, the specialized equipment is relatively large and costly, thereby confining it to clinical settings.

Hence, there is a need for a compact, personal device that would simplify these treatment methods and allow individuals to safely and effectively perform these treatments in the privacy of their home, allow longer treatments to be performed without the trouble of travelling to clinics or hospitals, and release professionals to perform other more complex treatments. Additionally, there is a need for a personal device that reduces the amount of substances and compositions, as well as the size of the light source used in treatment to allow the device to be used in a home setting.

SUMMARY

This application discloses a personal photodynamic therapy device which addresses the problems stated above. The photodynamic therapy device is configured for delivery of a photoactivatable composition to a treatment site. In one embodiment the photodynamic therapy device is a hand-held device that photoactivates the photoactivatable composition. In an alternative embodiment the device is a finger-mounted device. In some embodiments the photodynamic therapy device includes an illuminating member and an applicator cartridge detachably connected to the illuminating member.

In a first embodiment there is disclosed an applicator cartridge for delivery of a photoactivatable composition to a treatment site, having an applicator head, and a reservoir adapted to receive the photoactivatable composition therein. When pressure is applied to the applicator cartridge, the photoactivatable composition in the reservoir is pushed through the applicator head and delivered to the treatment site.

The applicator cartridge may have a mounting portion for mounting of the applicator cartridge on an illuminating member. The mounting portion may be threaded.

The applicator cartridge may have a removable cover member adapted to cover the applicator head. The removable cover member may be light impermeable.

The applicator cartridge may be light permeable, and it may be made from a flexible and/or inert material.

The applicator head may have an absorbent pad attached thereon.

The applicator cartridge may contain a photoactivatable composition, and it may be vacuum sealed.

In a second embodiment, there is disclosed a photodynamic therapy device for delivery of a photoactivatable composition to a treatment site, which comprises an illuminating member having an illuminating element and a power source electrically connected thereto; a mounting member, and an applicator cartridge detachably mounted on the mounting member. The mounting member may be threaded. The photodynamic therapy device may have a holding member.

The illuminating member may have a waveguide connected to the illuminating element. The waveguide may have at least one optical fiber.

The illuminating element may be a light emitting diode (LED). The light emitting diode (LED) may be emitting an actinic visible light. The light emitting diode (LED) may be emitting an actinic visible light from about 400 nm and about 600 nm. The illuminating element may be emitting an actinic continuous light or an actinic pulsed light.

The applicator cartridge in the photodynamic therapy device may contain the photoactivatable composition.

In a third embodiment, there is disclosed a method for tooth whitening comprising the steps of a) topically applying a photoactivatable composition using an applicator cartridge to at least one tooth, and b) treating said tooth of step a) to an actinic light for a time sufficient for the activation of the photoactivatable composition. The tooth may be whitened by being exposed to light for a period of between 5 seconds and 10 minutes, or for a period of between 5 minutes and 10 minutes or for a period of 1 minute, or for a period of 30 seconds.

In a fourth embodiment, there is disclosed a method for tooth whitening comprising the step of a) topically applying a photoactivated composition using a photodynamic therapy device to at least one tooth for a time sufficient for tooth whitening. The tooth may be whitened by being exposed to light for a period of between 5 seconds and 10 minutes, or for a period of between 5 minutes and 10 minutes, or for a period of 1 minute, or for a period of 30 seconds.

In a fifth embodiment, there is disclosed a method for wound healing comprising the steps of a) topically applying on a patient's skin a photoactivatable composition using an applicator cartridge, and b) treating said skin of step a) to an actinic light for a time sufficient for the activation of the photoactivatable composition.

In yet another embodiment, there is disclosed a method for wound healing comprising the step of a) topically applying on a patient's skin a photoactivated composition using a photodynamic therapy device for a time sufficient for stimulation of wound healing.

In yet another embodiment, there is disclosed a method for skin rejuvenation comprising the steps of a) topically applying on a patient's skin a photoactivatable composition using an applicator cartridge, and b) treating said skin of step a) to an actinic light for a time sufficient for the activation of the photoactivatable composition.

In yet another embodiment, there is disclosed a method for skin rejuvenation comprising the step of a) topically applying on a patient's skin a photoactivated composition using a photodynamic therapy device for a time sufficient for stimulation of skin rejuvenation.

In yet another embodiment, there is disclosed a method for treating a skin condition comprising the steps of a) topically applying on a patient's skin a photoactivatable composition using an applicator cartridge according, and b) treating said skin of step a) to an actinic light for a time sufficient for the activation of the photoactivatable composition.

In yet another embodiment, there is disclosed a method for treating a skin condition comprising the step of a) topically applying on a patient's skin a photoactivated composition using a photodynamic therapy device for a time sufficient for treating the skin condition.

In yet another embodiment, there is disclosed a method for full mouth disinfection and/or photodynamic assisted oral treatment of a patient comprising the steps of a) applying in a patient's mouth a photoactivatable composition using an applicator cartridge, and b) treating said mouth of step a) to an actinic light for a time sufficient for the activation of the photoactivatable composition.

In yet another embodiment, there is disclosed a method for full mouth disinfection and/or photodynamic assisted oral treatment of a patient comprising the step of a) topically applying in a patient's mouth a photoactivated composition using a photodynamic therapy device for a time sufficient for effecting full mouth disinfection.

In yet another embodiment, there is disclosed a method for healing neuropathic related skin lesions comprising the steps of a) topically applying on a patient's lesion a photoactivatable composition using an applicator cartridge, and b) treating said lesion of step a) to an actinic light for a time sufficient for the activation of the photoactivatable composition.

In yet another embodiment, there is disclosed a method for healing neuropathic related skin lesions comprising the step of a) topically applying in a patient's lesion a photoactivated composition using a photodynamic therapy device for a time sufficient for stimulating healing of the lesion.

The exposure to actinic light may be for a period of between 60 seconds and 5 minutes, or for a period of between 60 seconds and 5 minutes per $cm^2$ of an area to be treated. The actinic light may be visible light having a wavelength between about 400 nm and about 600 nm.

Definitions

The following terms are defined below.

The term "actinic light" is intended to mean light energy emitted from a specific light source (lamp, LED, or laser) and capable of being absorbed by matter (e.g., the photoactivator defined below) and produce an identifiable or measurable change when it interacts with it; for example an identifiable change could be a change in the color of the photoactivator used (e.g., from red to transparent).

The term "photoactivator" is intended to mean a chemical compound capable of absorbing actinic light. The photoactivator readily undergoes photoexcitation and then transfers its energy to other molecules, such as oxidants, thus enhancing or accelerating the dispersion of light, and enhancing or activating the oxidants present to release oxygen radicals in the reaction mixture. Examples of photoactivators include xanthenes derivatives, azo dyes, biological stains, carotenoids, etc.

The term "photodynamic therapy" (PDT) is intended to mean the combination of light and light sensitive agents, such as photoactivators in an oxygen-rich environment to provide treatment of various conditions. The photosensitive agent can absorb energy from photons (particles of light) and transfer this energy to surrounding oxygen molecules. Toxic oxygen species such as singlet oxygen and free radicals are thus formed. These chemicals are very reactive and can damage proteins, lipids, nucleic acids and other cellular components, and they can be used in several applications, including the treatment of cancers.

The term "time of exposure to actinic light" is intended to mean the length of time a treatment site such as tissue, skin, teeth or wounds are exposed to actinic light per application of actinic light.

The term "total time of exposure to actinic light" is intended to mean the cumulative time a treatment site is exposed to actinic light after several applications of actinic light.

The term "rejuvenation" is intended to mean the mitigation of the aging process, or any other processes (e.g., abrasion caused by a fall, burns, etc.) that may have damaged or caused an accumulation of damage to macromolecules, cells, tissues and organs, including the skin. Rejuvenation is the mitigation of any of such damage.

The term "photorejuvenation" is intended to mean the use of light for the mitigation of the aging process, or any other processes (e.g., abrasion caused by a fall, burns, etc.) that may have damaged or caused an accumulation of damage to macromolecules, cells, tissues and organs, including the skin.

The term "teeth whitening," also known as "teeth brightening," is intended to mean dental bleaching, also known as tooth whitening, which is a common procedure in general dentistry but most especially in the field of cosmetic dentistry. Teeth may need to be whitened since as a person ages the adult teeth often become darker due to changes in the mineral structure of the tooth, as the enamel becomes less porous. Teeth can also become stained by bacterial pigments, foodstuffs and tobacco. Certain antibiotic medications (like tetracycline) can also lead to teeth stains or a reduction in the brilliance of the enamel.

The term "wound" is intended to mean a type of injury in which skin is torn, cut or punctured (an open wound), or where blunt force trauma causes a contusion (a closed wound). In pathology, it specifically refers to an injury which damages the dermis of the skin.

The term "mouth" is intended to mean the entire oral cavity, which includes the lips, gingiva (gums), the hard and soft palate, the uvula, palatine tonsils, the teeth, the inside of the cheeks, the tongue and the papillae of the tongue.

The term "oral hygeine" is intended to mean the formation of biofilms which lead to diseases of the oral cavity such as periodontitis and gingivitis. Biofilms are the formation of a film by microbes on teeth or on chronic wounds.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

FIG. 5A illustrates a perspective view of an applicator cartridge according to one embodiment of the present invention.

DETAILED DESCRIPTION

Figure 1:
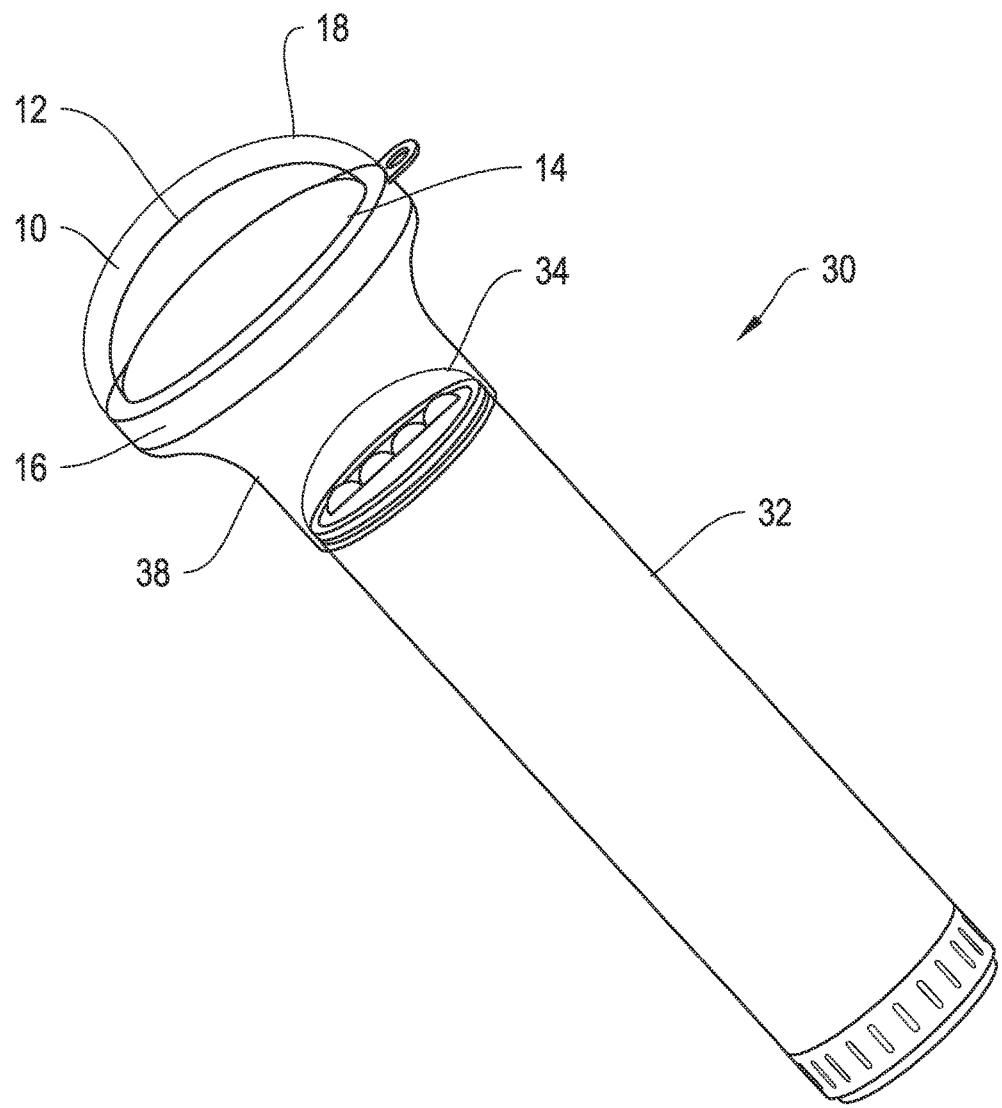
FIG. 1 illustrates a perspective view of a photodynamic therapy device according to one embodiment of the present invention.
Figure 2:
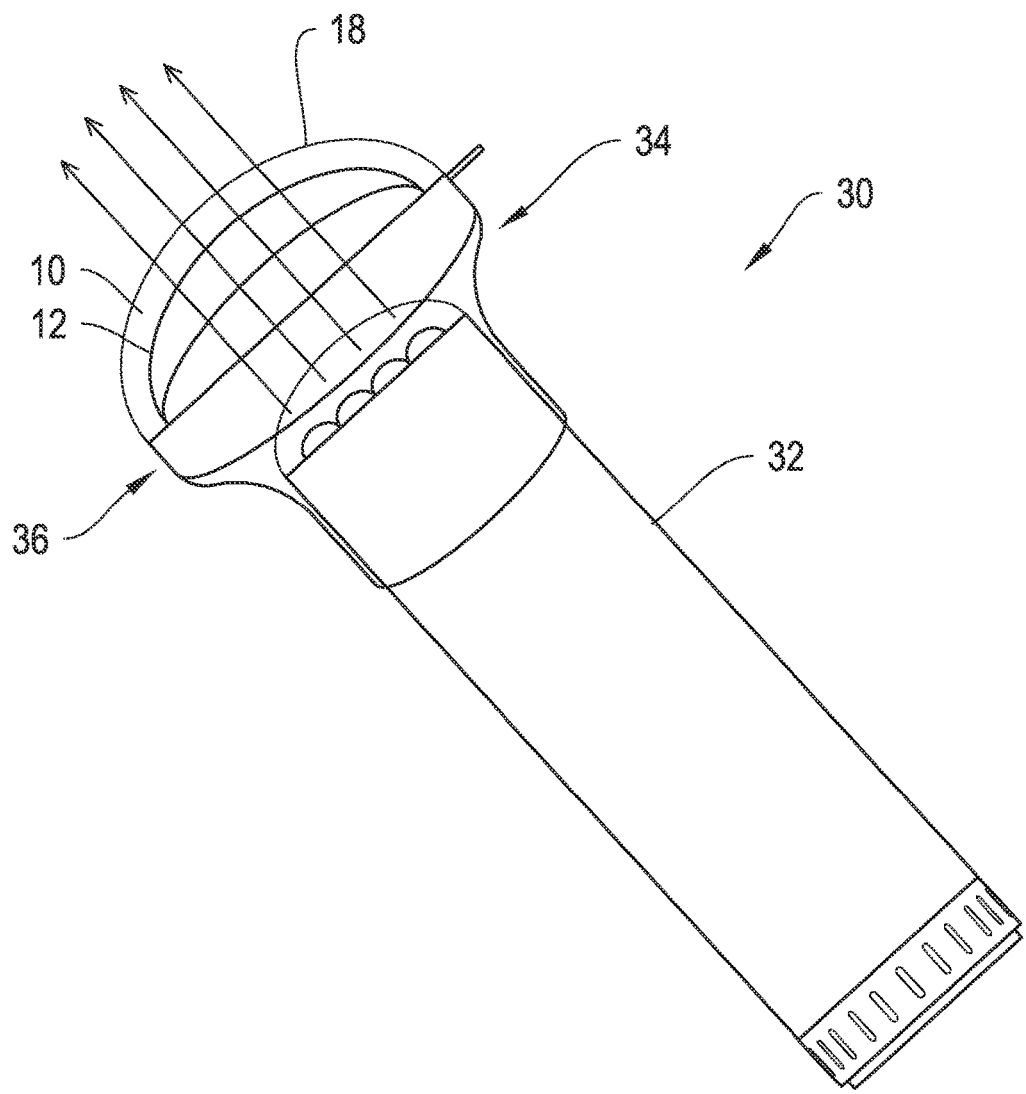
FIG. 2 illustrates a side view of a photodynamic therapy device according to one embodiment of the present invention.

Described herein are many examples of a photodynamic therapy devices and methods of use. The photodynamic therapy device is a compact hand-held device that may fit within the oral cavity. It will be noted that the systems and methods described herein may be implemented via any suitable combination of hardware (e.g., component parts). It will also be noted that examples of photodynamic therapy devices are described for ease of illustration, and that the systems and methods disclosed herein may be applied to any photodynamic therapy device. FIG. 1 illustrates an example of a photodynamic therapy device 30 according to an embodiment. Photodynamic therapy device 30 includes applicator cartridge 10 and illuminating member 32. Applicator cartridge 10 includes applicator head 12 and a reservoir 14, which is adapted to receive at least one component of a photoactivatable composition therein.

The photoactivatable composition may include one or more compositions. For example, the photoactivatable composition may include at least one of a photoactivator component (e.g., xanthenes derivatives, azo dyes, biological stains, carotenoids, etc.) and an oxidant component (e.g., hydrogen peroxide, carbamide peroxide, urea peroxide, benzoyl peroxide, peroxy acids, alkali metal percarbonates, etc.) that are mixed prior to treatment. Photoactivatable compositions are compositions that, in a general manner, are activated by irradiation with light of specific wavelength (i.e., actinic light). These compositions contain one or more photoactivator molecules which are activated by actinic light and accelerate the dispersion of light energy, which leads to the photoactivator carrying on a therapeutic effect on its own, or to the photochemical activation of other agents contained in the composition that could carry on a therapeutic effect (e.g., acceleration in the breakdown process of peroxide (an oxidant) when such compound is present in the composition). The included photoactivators are illuminated by photons of a certain wavelength and excited to a higher energy state. When the photoactivators' excited electrons return to a lower energy state, they emit photons with a lower energy level, thus causing the emission of light of a longer wavelength (Stokes shift). In the proper environment, much of this energy transfer is transferred to the other components of the photoactivatable composition or to the treatment site directly. Suitable photoactivators can be fluorescent dyes (or stains), although other dye groups or dyes (biological and histological dyes, food colorings, carotenoids) can also be used. Combining photoactivators may increase photo-absorbtion by the combined dye molecules and enhance absorption and photo-biomodulation selectivity. This creates multiple possibilities of generating new photosensitive, and/or selective photoactivator mixtures.

Photoactivatable compositions may contain other compounds, such as pH controlling agents (e.g., sodium acetate, sodium hydroxide), light diffracting agents (e.g., porcelain crystals, hydroxylapatite), healing factors (e.g., hyaluronic acid, glucosamine), chelating agents (e.g., EDTA, EGTA), lipolysis stimulating agents (e.g., caffeine), and/or hydrophilic gelling agents (e.g., glucose, celluloses). More information on the makeup of the photoactivatable composition and how they are mixed can be found in U.S. Patent Application Publication No. 2007/0128132, filed on Nov. 9, 2006, PCT Publication No. WO/2010/051636, filed on Nov.

6, 2009, PCT Publication No. WO/2010/051641, filed on Nov. 6, 2009, and PCT Application No. PCT/CA/2010/001134, filed on Jul. 19, 2010.

The Applicator head 12 may be made from any suitable oxidant resistive material for photodynamic therapy. Applicator head 12 may have multiple different surface types and sizes, or be made from various different materials depending on the intended use of the photodynamic therapy device 30. For example applicator head 12 may have a planar surface, it may have bristles or fingers extending from the surface, it may be smooth or textured, or may have any other suitable surface for applying the photoactivatable composition. In certain embodiments, the size of the applicator head 12 may increase depending on the size of the treatment area. For example, a large applicator head 12 may be used for treating large areas of the skin, and a small applicator head 12 may be used for treating teeth and/or gums. In certain embodiments, an applicator cartridge 10, with an applicator head 12 having different surface features, may be swapped in and out of the photodynamic therapy device 30 to make use of the surface features of the applicator head 12 (e.g., size, texture) for the intended therapy.

The surface of the applicator head 12 may function to provide a mechanical force to a treatment surface to clean or otherwise remove a biofilm from the treatment surface. In certain embodiments, a composition may be applied directly to the surface of applicator head 12. For example, composition stored in a tube may be applied directly onto the surface of the applicator head 12. In certain embodiments, the applicator head 12 may have one or more pores for passing a composition from the reservoir 14 through to a treatment surface. For example, when pressure is applied to the applicator cartridge, the photoactivatable composition in the reservoir 14 is pushed through the applicator head 12 and delivered to the treatment site.

Figure 3:
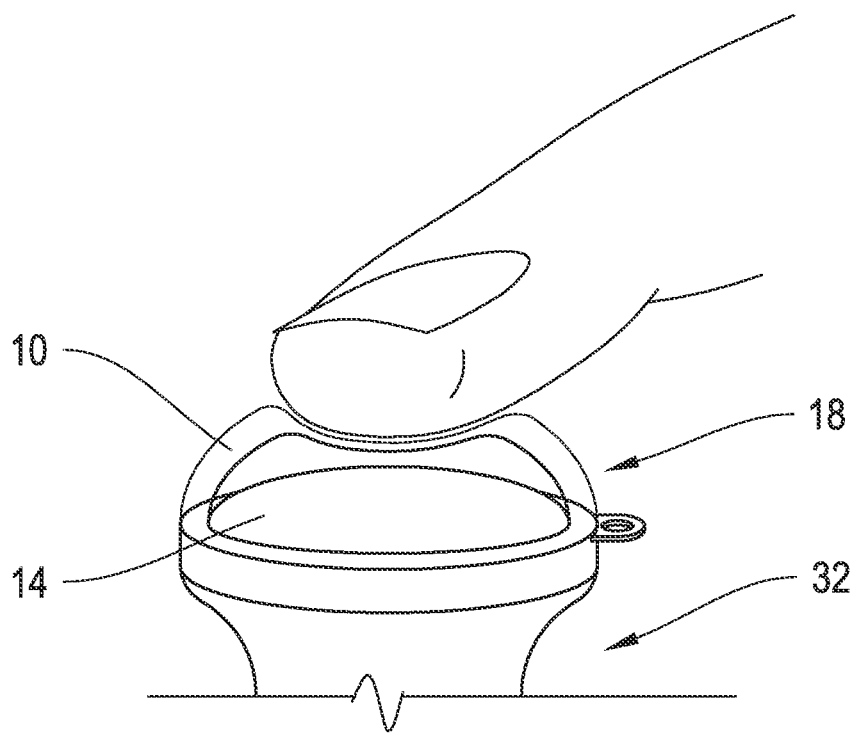
FIG. 3 illustrates a finger pressing down on an application cartridge according to one embodiment of the present invention.
Figure 4:
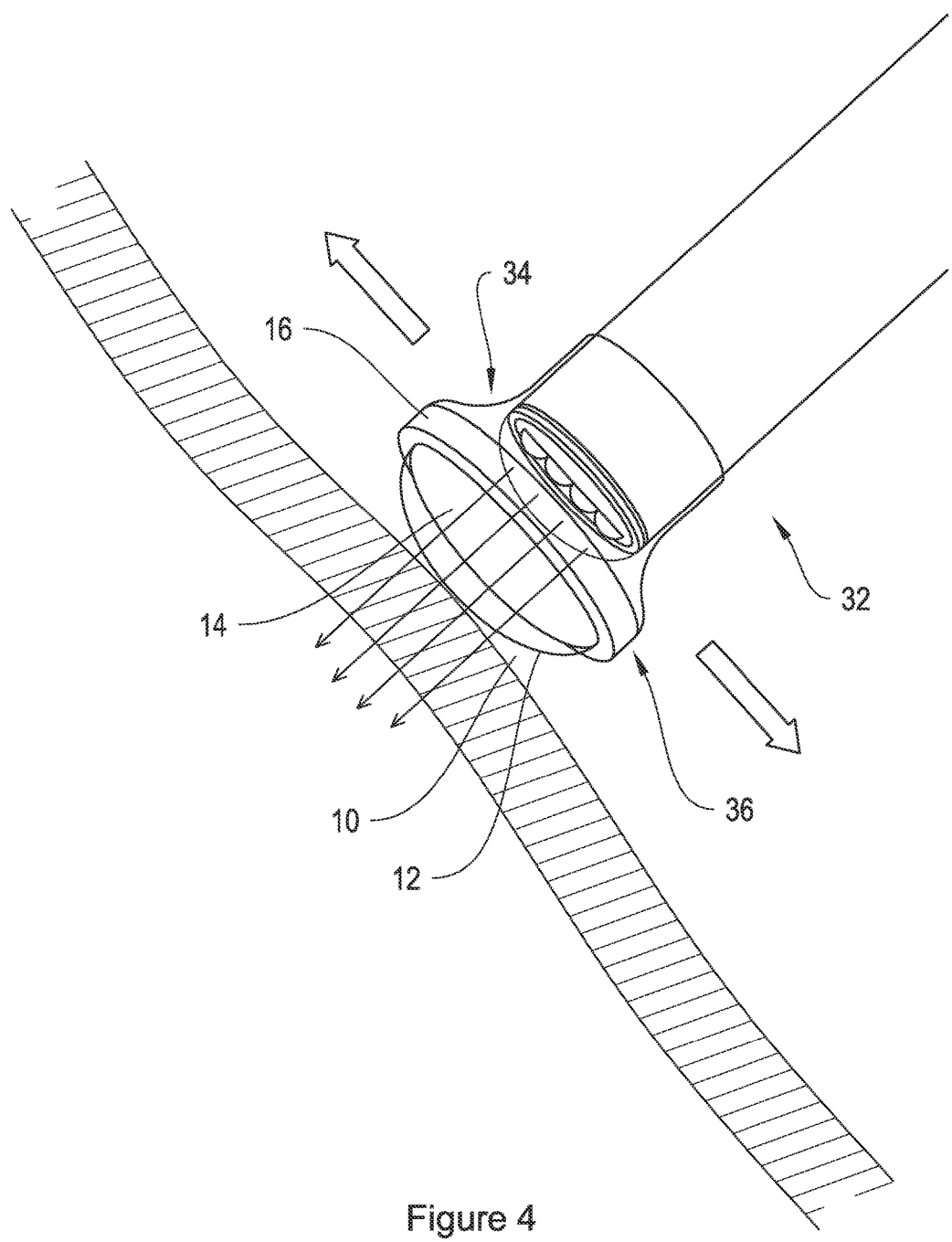
FIG. 4 illustrates a side view of a photodynamic therapy device according one embodiment of the present invention being rubbed on a surface.

Pressure may be applied by pressing the applicator cartridge 10 against the surface to which the composition is to be applied. FIG. 4 illustrates an example where the applicator head 12 of applicator cartridge 10 is pressed against a treatment surface. The pressure created by pressing the applicator head 12 against the treatment surface may cause the photoactivatable composition to be pushed out of the reservoir 14, through the applicator head 12 and onto the treatment surface. Additionally, as illustrated in FIG. 3, pressure may be applied by pressing the applicator cartridge 10 with fingers or other external means such as a pressure button on a holder for the cartridge.

In certain embodiments, at least one of an oxidant composition and an activator composition may be held in the reservoir 14, and the cover member 18 may be coated with at least one of an activator composition and an oxidant composition. When a force is exerted against the cover member 18, the cover member is pressed against reservoir 14 thereby mixing the oxidant composition with the activator composition prior to photoactivation and application to a treatment site. In certain embodiments, the cover member 18 may be made of a sufficiently flexible material that deforms upon application of a force. The oxidant composition may be a transparent, viscous gel that allows an actinic light to pass through the reservoir 14.

In certain embodiments, the removable cover member 18 may be placed over the applicator head 12, in order to prevent leakage of the photoactivatable composition from the applicator cartridge 10. The removable cover member 18 may be impermeable to light, to prevent exposure of light sensitive components of the photoactivatable composition in the reservoir 14 to ambient light, and preserve the composition in a dormant or inactive state. The removable cover member 18 may be fabricated from any suitable opaque or dark colored material, such as dark plastics.

In certain embodiments the applicator cartridge 10 may comprise a mounting portion 16, for mounting the applicator cartridge on a holder for the cartridge, or on an illuminating member 32, to photoactivate the photoactivatable composition contained in the reservoir 14. The mounting portion 16 may be threaded, or may include a clip or detent for receiving a clip. For example, the applicator cartridge 10 may be screwed on to an illuminating member 32 using a threaded mounting portion 16. In certain embodiments, the applicator cartridge 10 may be connected (e.g., by a clip) to a holder, such as an elongated stem or waveguide 38. The holder may then be connected to an illuminating member 32.

The applicator cartridge may be fabricated from any suitable oxidant resistive material so that it is not reactive with the photoactivatable composition enclosed therein. The applicator cartridge 10 may be fabricated from a light permeable material, such as any suitable polymeric films and/or plastic materials in order to allow the passage of actinic light from an illuminating element to the treatment site. Preferably, the material should be sufficiently flexible so as to allow deformation of the applicator cartridge 10 in order to facilitate extrusion of the photoactivatable composition enclosed therein, or allow mixing of the photoactivatable composition by simple repeated pressure thereupon.

Figure 5B:
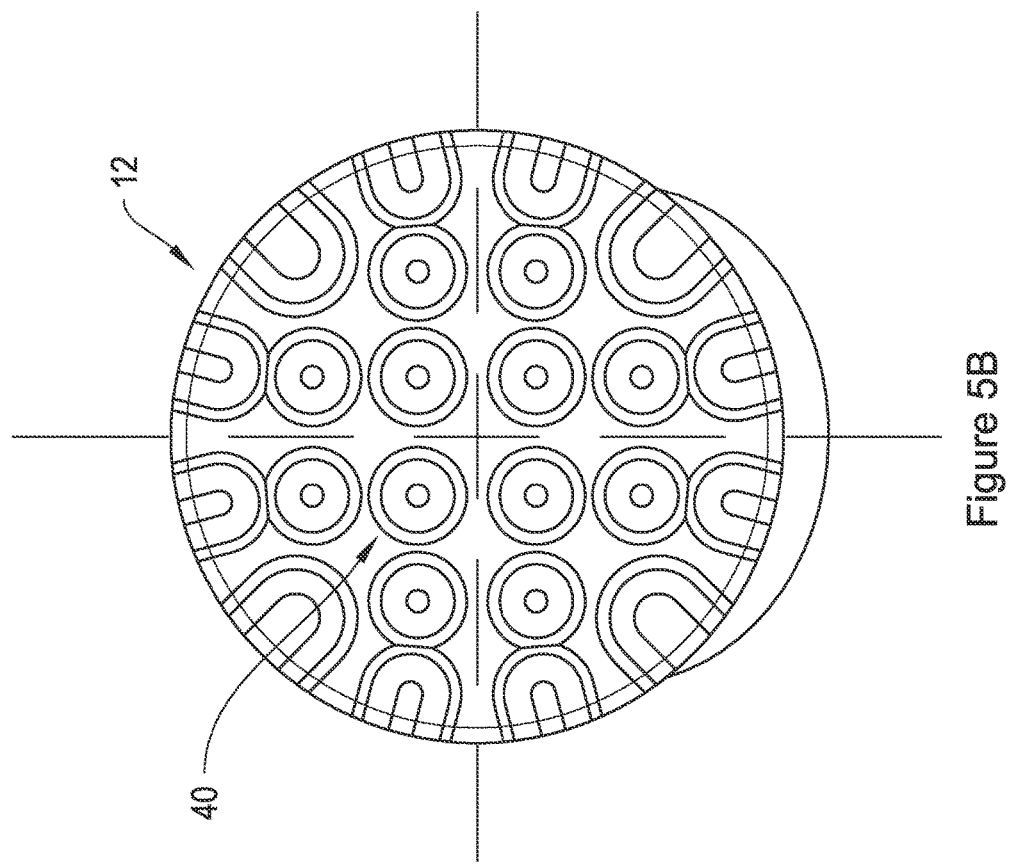
FIG. 5B illustrates a front view of the applicator head of an applicator cartridge according to one embodiment of the present invention.
Figure 5C:
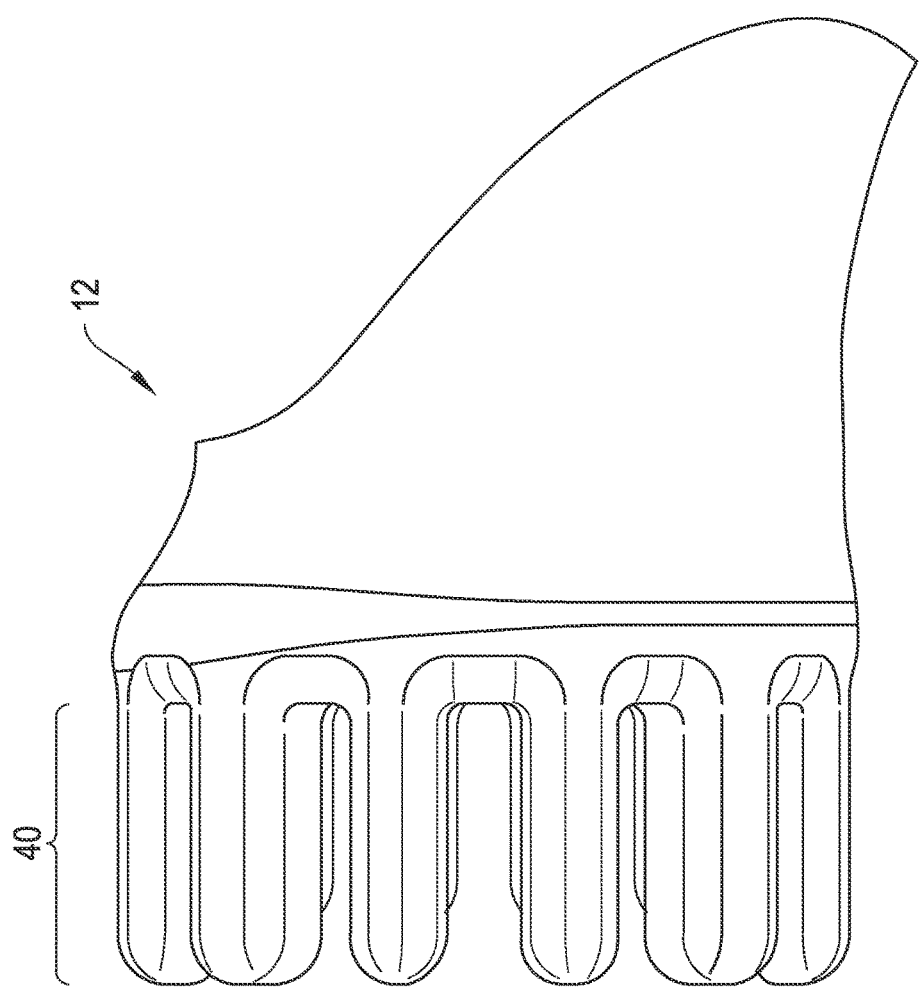
FIG. 5C illustrates a side view of the applicator head of an applicator cartridge according to one embodiment of the present invention.
Figure 6:
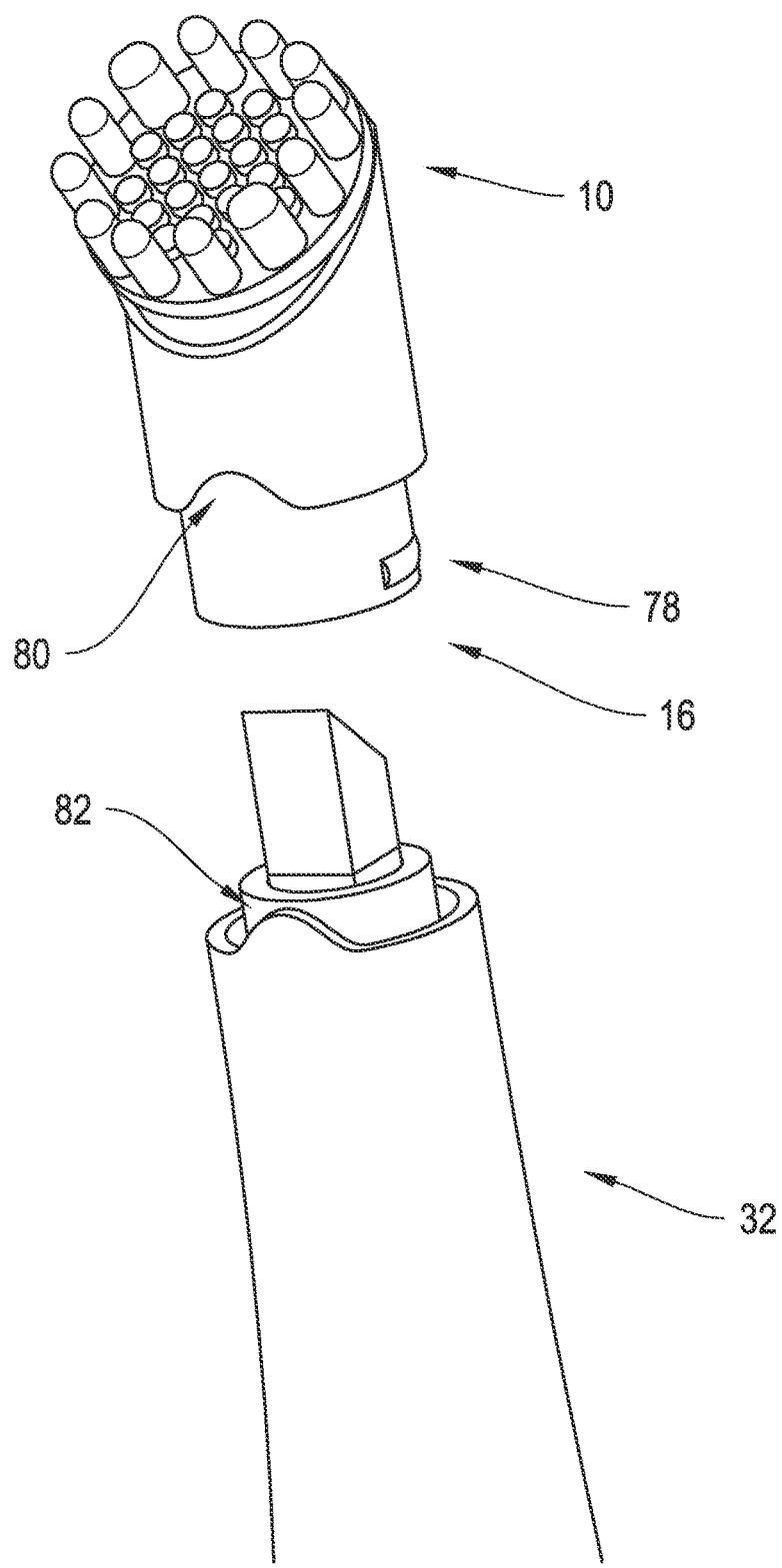
FIG. 6 illustrates an applicator cartridge mounting portion according to one embodiment of the present invention.
Figure 7A:
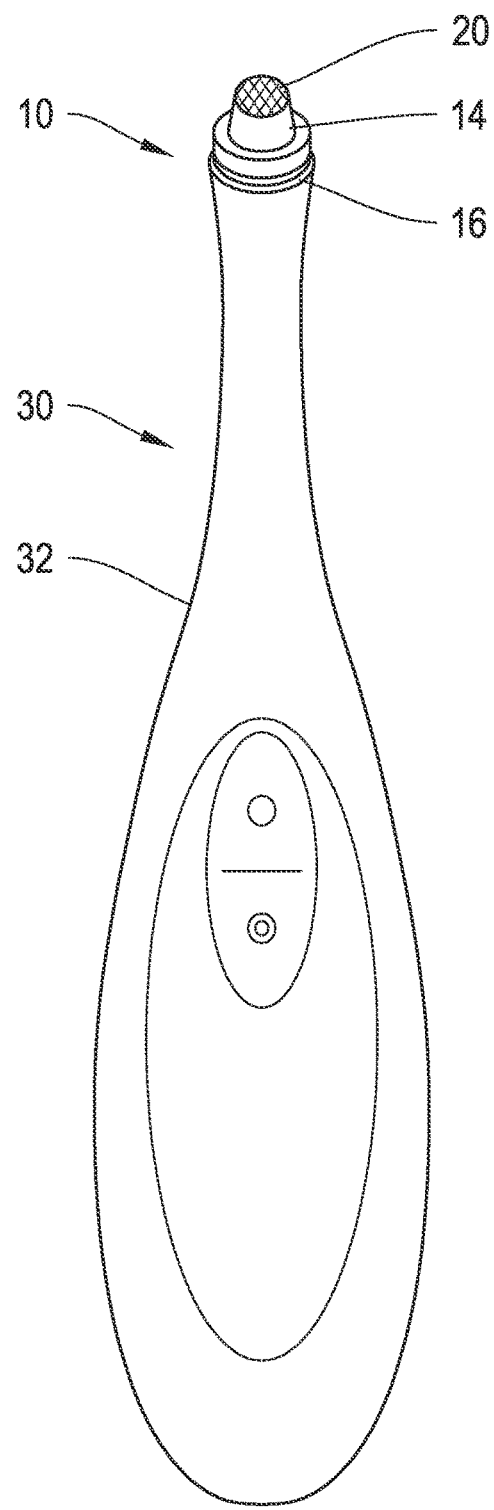
FIG. 7 illustrates a front view (7A) and a side view (7B) of a photodynamic therapy device, and an exploded side view of an applicator cartridge (7C) according to one embodiment of the present invention.
Figure 7B:
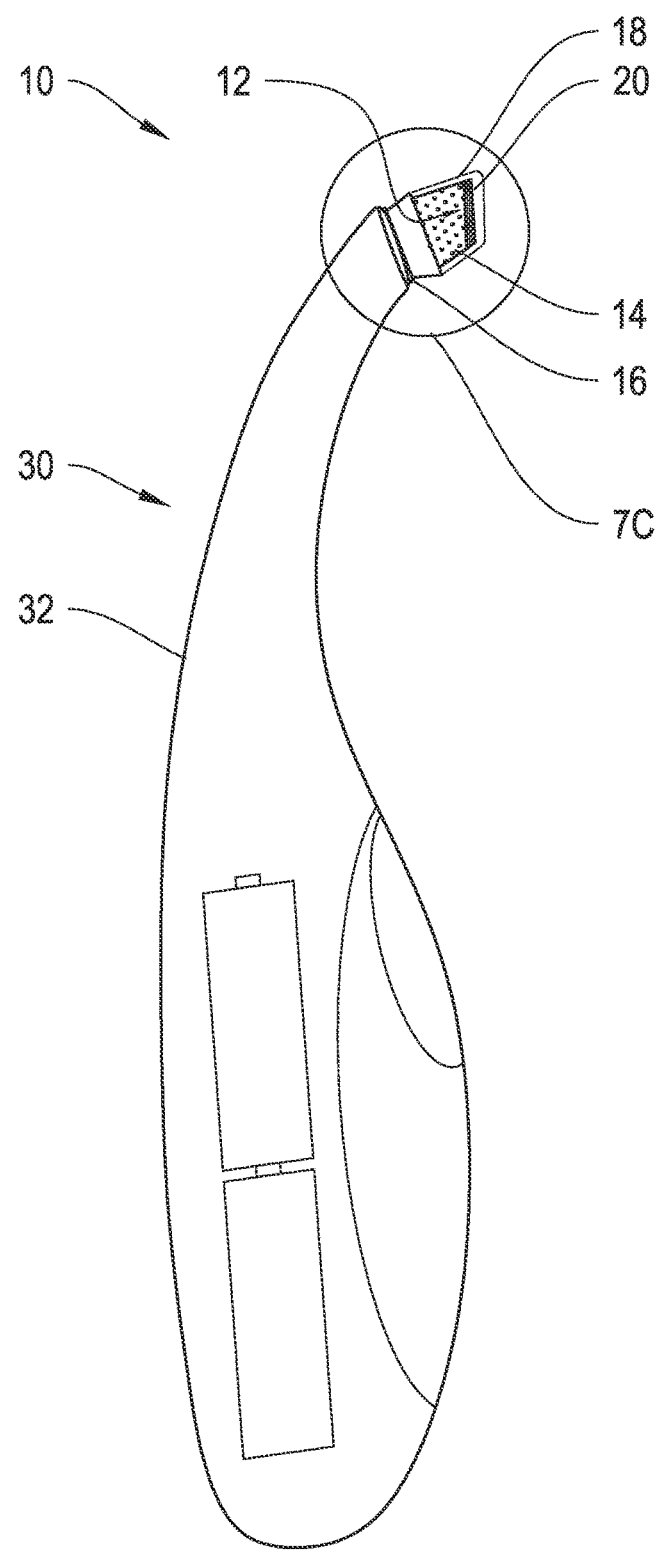
Figure 7C:
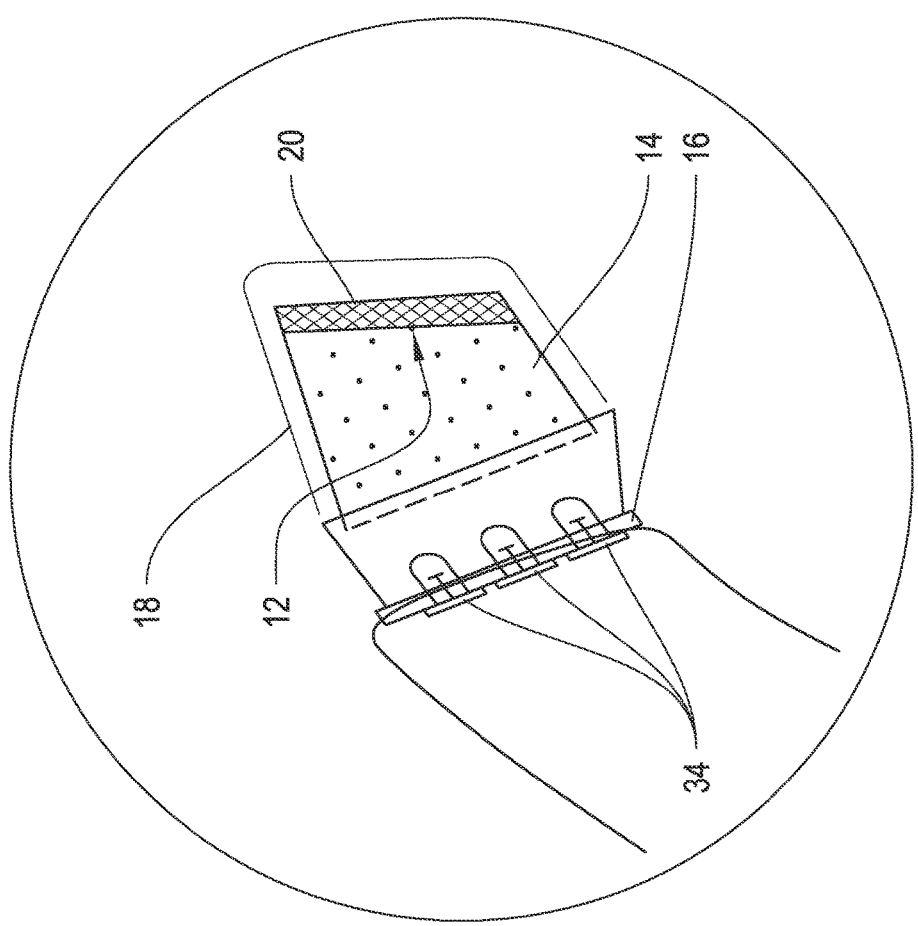

FIG. 5A shows an example of applicator cartridge 10 according to an embodiment. The applicator cartridge 10 of FIG. 5A includes a plurality of fingers 40 on the applicator head 12, a rigid neck 42, an integral light pipe within rigid neck 42, and a snap interface 16. The plurality of fingers 40, may be made of any suitable flexible material which allows actinic light to pass through, such as silicone. The plurality of flexible fingers may provide a dual function of supplying a photoactivatable composition to a treatment site, and applying a mechanical force to the treatment surface. The mechanical force may function to remove a biological film, and to clean the treatment surface or prepare it for application of the photoactivatable composition. Snap interface 16, allows applicator cartridge 10 to be removably connected to a cartridge holder or to an illuminating member. For example, snap interface 16 may be removably connected to one end of a stem 50. The other end of stem 50 may be removably connected to an illuminating member 32. For example, FIG. 6 shows an example of an applicator cartridge 10 having clip detent 78, and recess 80. Applicator cartridge 10 may be connected to illuminating member 32 (or any other suitable cartridge holder, such as stem 50) by sliding the end of the cartridge over the exposed light guide to snap into place. Detent 78 may be secured by a snap holder in light guide 32 to hold the applicator cartridge 10 in place. Additionally, recess 80 may be lined up with convex protrusion 82 to ensure proper orientation of the applicator cartridge 10. As shown in FIG. 7, the applicator cartridge 10 may also be fitted with an absorbent pad 20, placed proximately, or over the applicator head 12. The absorbent pad 20 is able to absorb the extruded photoactivatable composition and facilitate application on any treatment surfaces. The absorbent pad 20 may be a cotton pad, or any absorbent or sponge-like material, from natural or synthetic origin resistant to oxidizing material. The consistency of the absorbent pad 20 material is not to interfere with the propagation of actinic light from the illuminating element. The absorbent pad 20, when rubbed against the treatment area produces friction which enhances the cleaning of the treatment area. This is particularly advantageous in teeth bleaching applications, where the additional mechanical energy being input in the system results in more efficient cleaning and increases the bleaching of the teeth. The removable cover member 18 may press against the absorbent pad 20 and compress it.

In certain embodiments, the applicator cartridge 10 may be sold empty, to be filled with photoactivatable composition prior to application, or it may be sold containing a photoactivatable composition suitable to a specific treatment. Furthermore, the applicator cartridge 10 may be vacuum sealed to prevent reaction of compounds found in the photoactivatable composition (e.g., hydrogen or carbamide peroxide) enclosed therein. In certain embodiments, the applicator cartridge 10 may be disposed after one or more uses and replaced by another applicator cartridge. In certain embodiments, the applicator cartridge 10 may be refilled with composition as necessary. The applicator cartridge 10 may be color coded, or otherwise appropriately identified to provide an indication of what composition is inside.

In certain embodiments, the applicator cartridge 10 may be used alone, to dispense a composition onto a treatment site, which is then irradiated with an external light source. Alternatively, the applicator cartridge 10 may be used in combination with a photodynamic therapy device 30, which comprises an illuminating member 32 containing an illuminating element 34, which is electrically connected to a power source. The illuminating member also comprises a mounting member 36, which is adapted to receive the applicator cartridge 10, preferably by mounting the applicator cartridge 10 through the mounting portion 16. After usage, the spent applicator cartridge 10 may be detached from the photodynamic therapy device 30 and refilled, or replaced with a fresh applicator cartridge 10.

In certain embodiments, the illuminating member 32 may comprise a waveguide 38, in order to separate the applicator cartridge 10 from the illuminating element 34, and/or concentrate the actinic light for a more robust activation of the photoactive composition. The waveguide 38 may contain a light pipe, one or more optical fibres, or any other suitable waveguide known to those of skill in the art. The illuminating member 32 may be designed in any suitable shape to promote use of the photodynamic therapy device 32. For example, the illuminating member 32 may also serve as a handle to be held by a user while using the photodynamic therapy device 32. The illuminating element 34 may be any suitable source of light, such as a light emitting diode, halogen, plasma arc lamp, or laser. The primary characteristic of suitable sources of actinic light will be that they emit light in a wavelength (or wavelengths) appropriate for activating the one or more photoactivators present in the composition. In certain embodiments the illuminating element 34 is spaced anywhere from 0-10 cm away from the applicator cartridge 10. For example, the illuminating element 34 may be spaced approximately 2 cm away from the applicator head so that the illuminating element is close enough to the photoactivatable composition to effectively photoactivate it. In certain embodiments, the illuminating element 34 emits actinic light in the visible spectrum. For example, the illuminating element 34 may emit actinic light in the 400 to 600 nm wavelength range to activate the composition. In certain embodiments, light sources that produce light outside of the visible region (e.g., infrared and ultraviolet) may be used. For example, certain compositions may require interaction with light in a particular spectrum to be photoactivated. Furthermore, the source of actinic light should have a suitable power density. Suitable power densities for non-collimated light sources (LED, halogen or plasma lamps) are in the range from about 50 mW/cm$^2$ to about 2000 mW/cm$^2$. Suitable power density for laser light sources are in the range from about 50 mW/cm$^2$ to about 2000 mW/cm$^2$. The illuminating element 34 may emit a continuous beam of actinic light, or it may emit a pulsed beam of actinic light. In certain embodiments, the illuminating element may be adjustable to produce varying power outputs. For example, current to the light source may be limited to control light output. The current may be limited in varying steps. For example there may be 5 light output positions: 200 mA, 300 mA, 400 mA, 500 mA, 600 mA. It will be recognized by those of skill in the art that any number of light output positions may be used. In certain embodiments, a continuous range may be used for the light output levels. The illuminating element 34 may be powered by any suitable power source such as one or more batteries, one or more capacitors, an outlet, or any other suitable power source known to those of skill in the art. The power source may be contained within the photodynamic therapy device 30 or the power source may be located external to the photodynamic therapy device 30.

In use and according to one embodiment, an applicator cartridge 10 may be fitted onto the illuminating member 32, and upon turning on the illuminating element 34, the actinic light activates at least a portion of the mixed photoactivatable composition, including the activating composition and the oxidant gel from the reservoir 14. The user or patient then applies the applicator head onto the treatment site, and dispenses the photoactivated composition to the treatment site, which will then carry on its therapeutic purpose in the presence of light emitted from the illuminating element 34. In certain embodiments, the photoactivatable composition may be applied to the surface of the applicator cartridge 10, and upon turning on of the illuminating element 34, the actinic light activates the composition on the surface of the applicator cartridge 10. The user then applies the applicator head to the treatment site. The photoactivatable composition may be photoactivated by the actinic light source prior to, as well as during, application to a treatment site.

Figure 8:
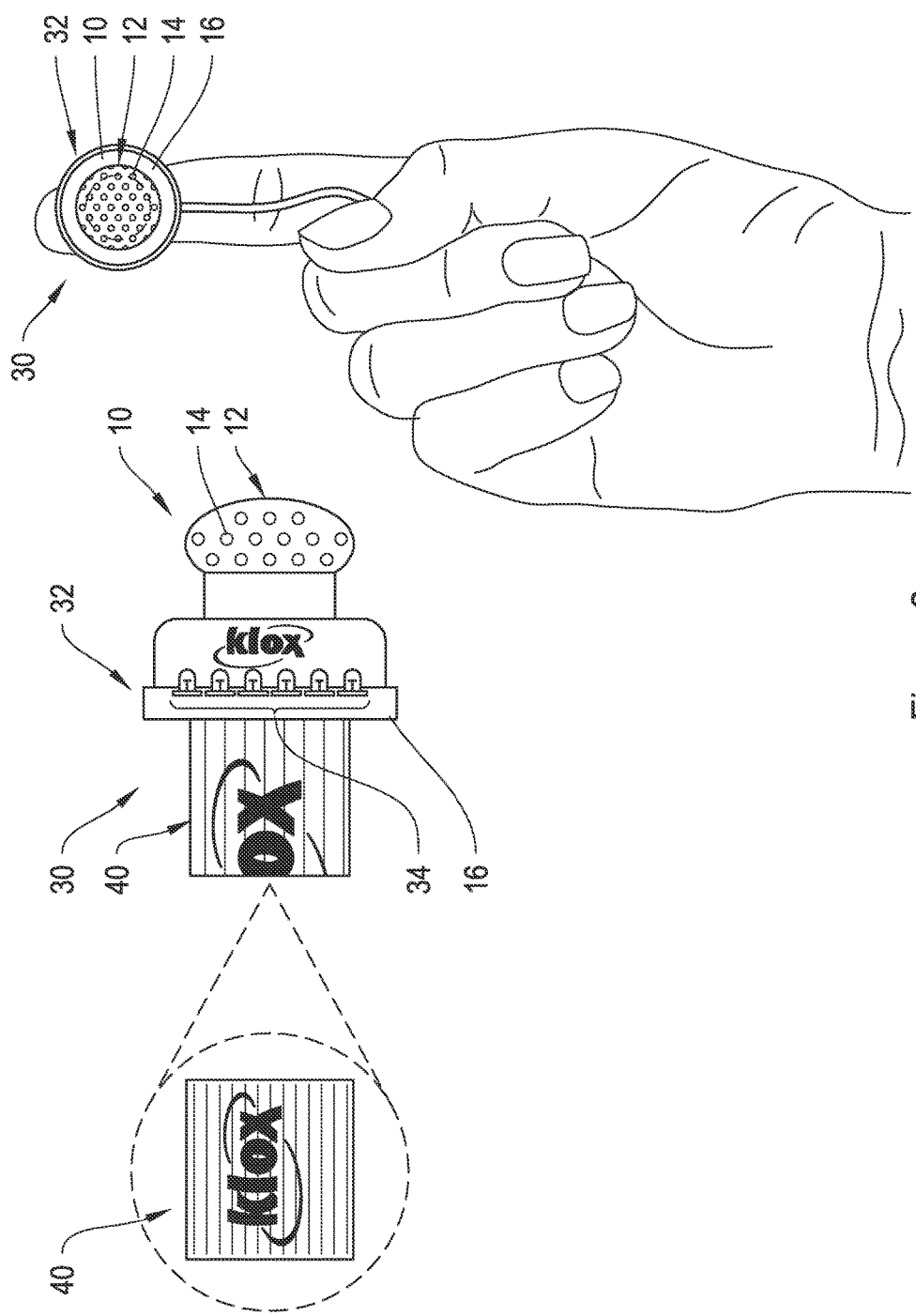
FIG. 8 illustrates a photodynamic therapy device according to one embodiment of the present invention.

FIG. 8 illustrates an example of a finger-mounted photodynamic therapy device 30. The finger-mounted photodynamic therapy device 30 may include a holding member 40, so that the photodynamic therapy device 30 may be, finger-mounted, or hand mounted. The holding member 40 may be in the shape of a loop so that one or more fingers may fit through to grasp the photodynamic therapy device 30. The photodynamic therapy device 30 of FIG. 8 may also include an illuminating member 32 including illuminating element 34, applicator cartridge 10, and mounting portion 16, for removably mounting the applicator cartridge 10 to the illuminating member 32. In the example shown in FIG. 8, the illuminating element 34 may be illuminated by pressing on the back of illuminating member 32, or may be illuminated by an external actuator. In certain embodiments, the finger-mounted photodynamic therapy device 30 may include a port to recharge the power source via an external charger. For example, the device may include a USB port charging the power source.

Figure 9A:
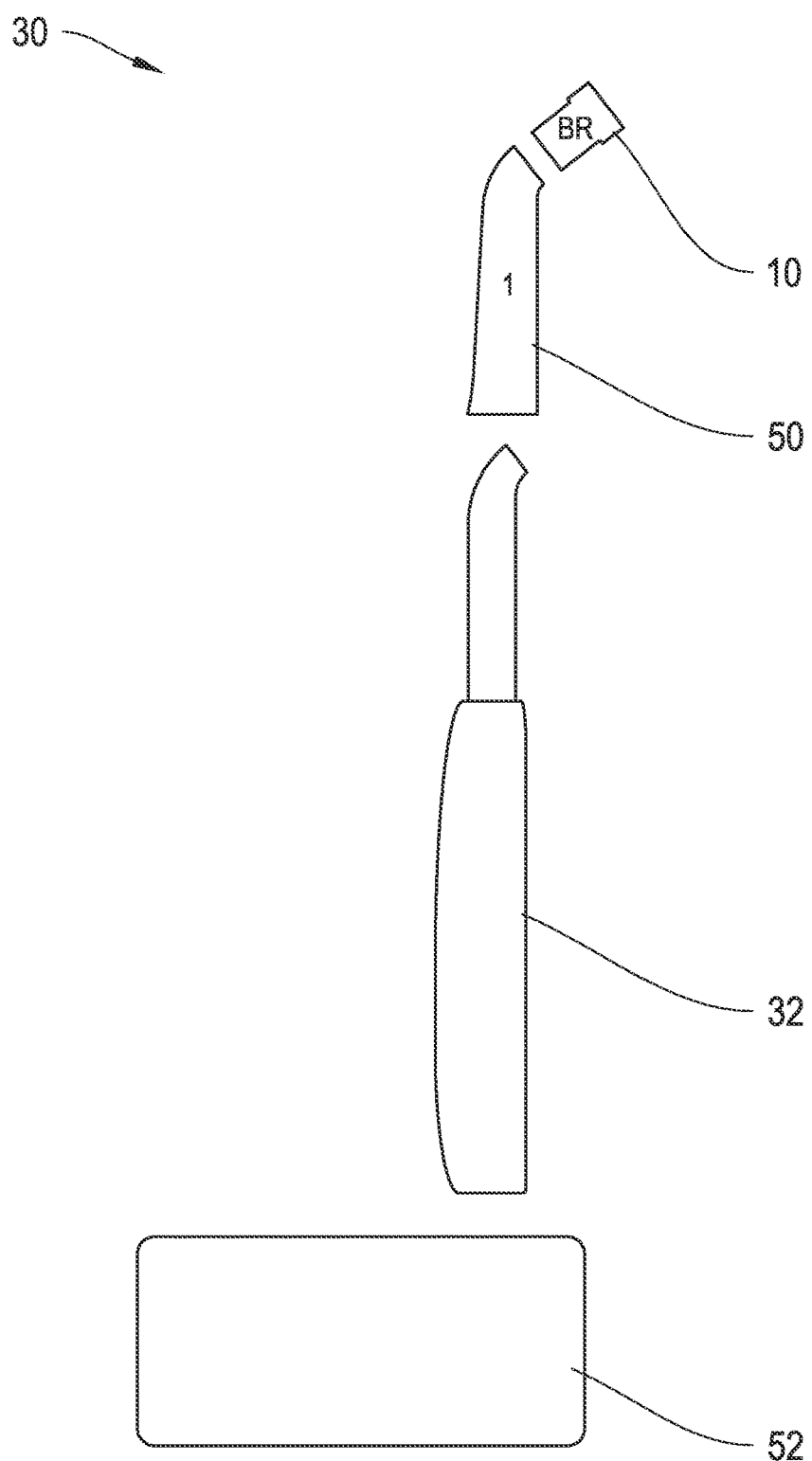
FIG. 9A illustrates a photodynamic therapy device according to one embodiment of the present invention.

FIG. 9A shows an example of a photodynamic therapy device 30 according to one embodiment. The photodynamic therapy device 30 of FIG. 9A includes an applicator cartridge 10, an illuminating member 32, a stem 50 for connecting the applicator cartridge 10 to the illuminating member 32, and base 52. The applicator cartridge 10 removably connects to stem 50, for example, by using a clip mechanism, threaded connector, snap connector, or any other suitable connection mechanism known to those of skill in the art. The stem 50 may slide over the end of the illuminating member 32 and connect to the illuminating member using a clip mechanism, threaded connector, snap connector, or any other suitable connection mechanism known to those of skill in the art.

Figure 9B:
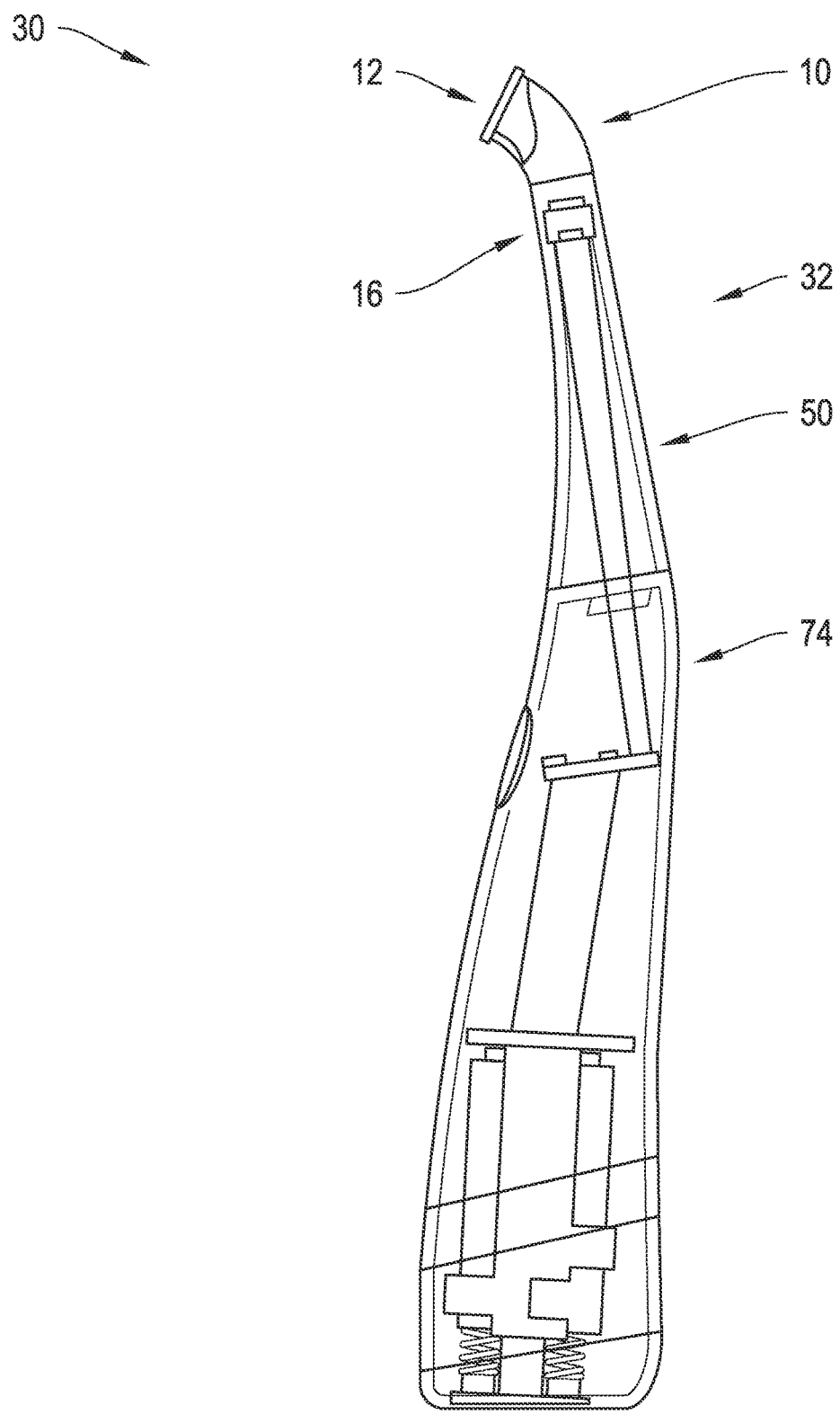
FIG. 9B illustrates a side view of a photodynamic therapy device according to one embodiment of the present invention.
Figure 9C:
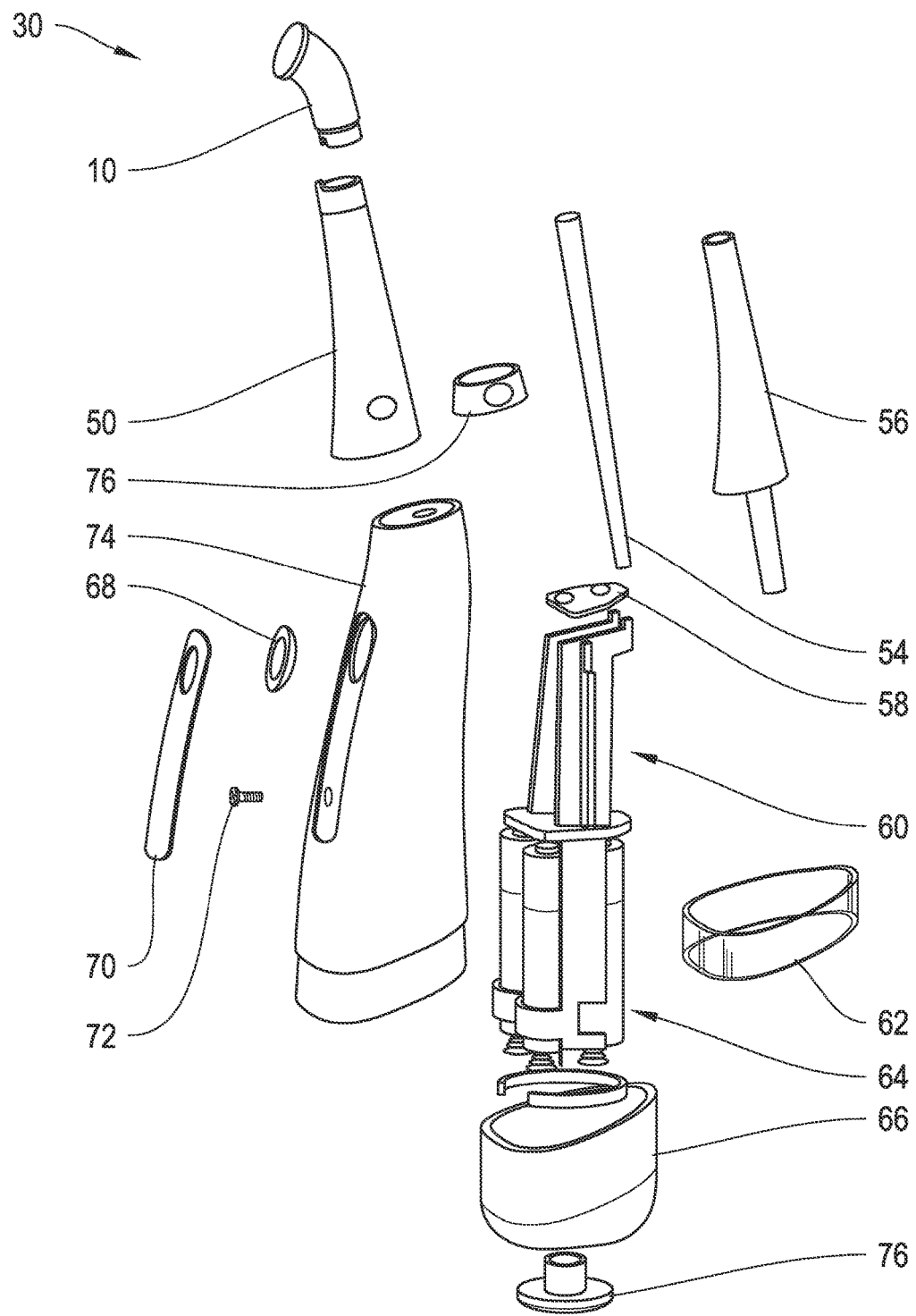
FIG. 9C illustrates an exploded view of a photodynamic therapy device according to one embodiment of the present invention.

In certain embodiments, different applicator cartridges 10 containing different compositions may be swapped in and out of photodynamic therapy device 30. In certain embodiments, the stem 50 may be individualized for one or more users. For example, the stem 50 may be color-coded or otherwise labeled to indicate a distinct stem. In certain embodiments, illuminating member is designed to stand upright on a flat surface of to fit in base 52. Additionally, illuminating member 32 may be designed to have a "swan" shape as shown in FIGS. 9A-9C, to promote more efficient therapy for certain treatment sites (e.g., rear teeth). In certain embodiments, base 52 acts as a simple holder to hold the photodynamic therapy device 10 while it is not in use, or while it is being prepared for use. Additionally, base 52 may hold other components of the photodynamic therapy device 30, such as extra applicator cartridges 10, stems 50, and/or tubes containing photoactivatable compositions. In certain embodiments, the base 52 may be used to recharge the photodynamic therapy device 30. For example, the base 52 may include an induction coil for inductively charging batteries, capacitors, or other power sources connected to the photodynamic therapy device 30.

FIG. 9B shows an illustrative example of a photodynamic therapy device according to an embodiment. The photodynamic therapy device 30 of FIG. 9B includes an applicator cartridge 10, and an illuminating member 32. The applicator cartridge 10 includes an applicator head 12. The applicator head 12 may include any texture, size or surface feature as described above. The illuminating member 32 includes a stem 50 and a body 74. The stem 50 may house a light guide, such as a light pipe, fiber optics cables or any other suitable light guide. In certain embodiments, the body 74 may include an illuminating element 34, control circuitry, a power source (e.g., batteries), and an internal frame supporting the elements within the body 74.

FIG. 9C shows an illustrative example of an exploded version of the photodynamic therapy device 30 of FIG. 9B. In addition to what is illustrated in FIG. 9B, the photodynamic therapy device 30 includes a light pipe 54, a light pipe protector 56, a Printed Circuit Board (PCB) 58 including an illuminating element 34, an internal frame 60, a seal ring 62, batteries 64, a battery access cap 66, an actuator button 68, a button plate 70, an internal frame screw 72, and a removal screw 76. The light pipe 54 is connected to the illuminating element 34 and concentrates light from the illuminating element to the applicator cartridge 10. The light pipe 54 is surrounded by a light pipe protector 56 which connects to the body 74. The stem 50 may be slid over the light pipe protector 56 and connected to the body 74. The PCB 58 may include circuitry for driving the illuminating element 34. For example, if the illuminating element is an LED, the PCB 58 includes LED drive circuitry to power the LED. The PCB 58 is secured in place by an internal frame 60 which is secured inside the body 74 by the seal ring 62, battery access cap 66, and the removal screw 76. The batteries 64, may be conveniently inserted and removed by removing and replacing the battery access cap 66. The PCB 58 and the illuminating element 34 may be controlled by a user through actuator button 68. For example, when a user activates actuator button 68, the illuminating element 34 may be illuminated to photoactivate the composition within or on the surface of the applicator cartridge 10.

In certain embodiments, the photodynamic therapy devices of FIGS. 9B and 9C are designed particularly for teeth brightening, however the devices depicted in FIGS. 9B and 9C, or any variation of them, may be used for applications other than teeth brightening as described in more detail below.

Figure 10A:
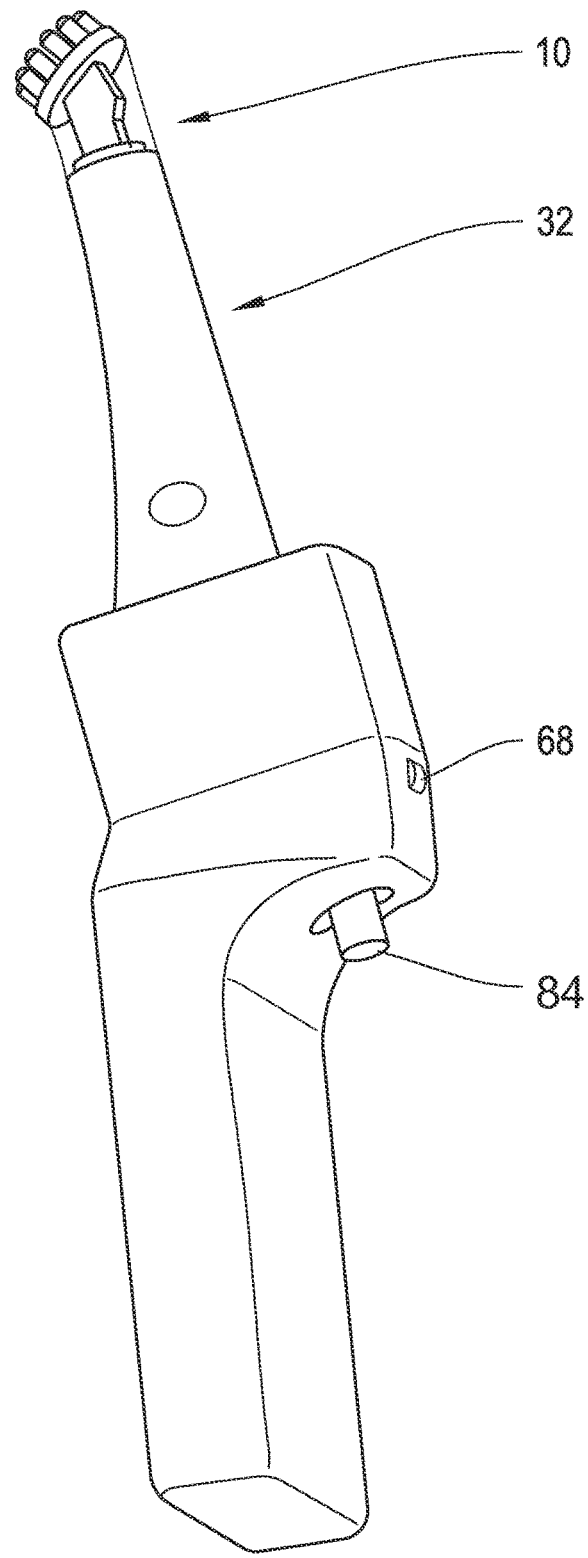
FIGS. 10A and 10B illustrate side views of a photodynamic therapy device according to one embodiment of the present invention.
Figure 10B:
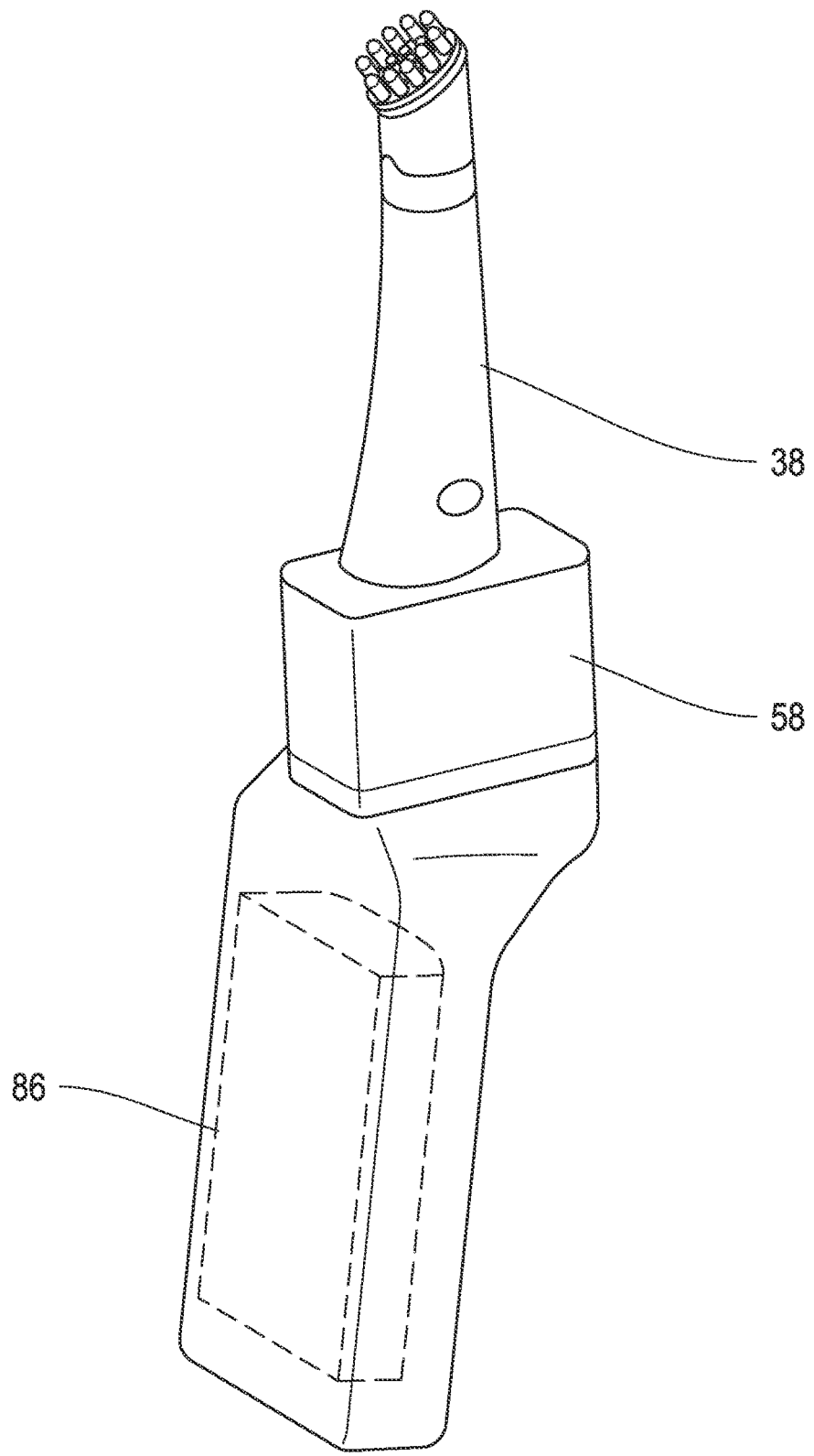

FIGS. 10A and 10B show an illustrative example of a photodynamic therapy device 30 according to an embodiment. The photodynamic therapy device 30 includes a cartridge 10, an illuminating member 32, a light guide 38, a PCB 58, a battery holder 86, an actuator 68, and a rotary switch 84. In the example illustrated in FIGS. 10A and 10B, the rotary switch 84 may be used to variably control the output of an illuminating element within illuminating member 32. For example, the rotary switch 84, may be a current regulator for controlling the amount of current between a power source and the illuminating element. It will be understood by those of skill in the art that any suitable mechanism may be used in place of the rotary switch 84, to control the output of an illuminating element.

The photodynamic therapy device 30, as described in the various embodiments above, may be used to whiten teeth. For example, a photoactivatable composition comprising one or more suitable photoactivator compositions, along with a source of peroxide may be used for whitening teeth. The activation of the peroxide by actinic light dispersed by the photoactivating agent within the composition leads to a prompt bleaching of the teeth.

The photodynamic therapy device 30, as described in the various embodiments above, may be used in conjunction with a suitable photoactivatable composition to treat injuries to the different layers of the skin, including incisions, lacerations, abrasions, puncture wounds, penetrations wounds, gunshot wounds, contusions, hematomas and crushing injuries. Lesions to mucosae may also be treated with the composition of the present invention, which may be used, for example, to treat pathological lesions of the oral mucosa, such as periodontitis, ulcers, and cold sores (orofacial herpes).

The photodynamic therapy device 30, as described in the various embodiments above, may be used in conjunction with a suitable photoactivatable composition to treat photoaging, fine lines, pigmentation, tactile roughness, sallowness damages caused by normal aging, as well as premature aging of the skin caused by exposure to the sun. These damages include but are not limited to photoaging, hyperpigmentation, large pores, skin irregularities, fine lines, and dark skin discoloration, hair growth (hirsutism), and sun damage, pigmented lesions (e.g., melanocytic proliferations, reticular melanotic hypermelanoses), hyperpigmented lesions (e.g., post-traumatic hyperpigmentation), wrinkles, sagging skin, and scars.

The photodynamic therapy device 30, as described in the various embodiments above, may also be used to treat a wide array of skin conditions. These include but are not limited to acne and acne scars, rosacea, nevi (blemish on the skin), Mongolian spots, such as Becker's nevus, blue nevus, congenital nevus, pigmented nevus (mole), nevus of Ota and Ito, pigmented spindle cell nevus, and dysplastic nevus may also be treated with the composition.

Visible vascular lesions to the skin may also be treated with the photodynamic therapy device 30, as described in the various embodiments above, in conjunction with a suitable photoactivatable composition. These include but are not limited to matted telangiectasia, lentigines, cherry angioma (a.k.a. "De Morgan spots", and "Senile angiomas"), spider angioma (a.k.a. nevus araneus, spider nevus, or vascular spider), vascular lesions such as vascular birthmarks, blue, red or purple port wine stains, red or blue facial and leg veins (a.k.a. spider veins).

The photodynamic therapy device 30, as described in the various embodiments above, may be used in conjunction with a suitable photoactivatable composition to treat neuropathic lesions caused by any one of polyneuropathy, mononeuropathy, mononeuritis multiplex and autonomic neuropathy. These especially include, but are not limited to Herpes zoster (a.k.a. shingles).

The photodynamic therapy device 30, as described in the various embodiments above, may be used in conjunction with a suitable photoactivatable composition to effect full mouth disinfection (e.g., containing a source of oxidant such as hydrogen peroxide and/or carbamide peroxide). The application cartridge 10 and the photodynamic therapy device 30 may be used in conjunction with a suitable photoactivatable composition to treat periodontal diseases caused by bacterial infection. Oral diseases, such as gingivitis, periodontitis, periodontal disease, oral thrush, lichen planus, and stomatitis may also be treated.

The duration of the exposure to actinic light will be dependent on the surface of the treated area, and on the type of lesion, trauma or injury that is being treated. The photoactivation of the composition may take place within seconds or even fragment of seconds, but a prolonged exposure period may be beneficial to exploit the synergistic effects of the absorbed, reflected and reemitted light on the composition of the present invention and its interaction with the treatment site. In one embodiment, the time of exposure to actinic light of the tooth, tissue, skin or wound on which the photoactivated composition has been applied is a period between 1 second and 10 minutes. In another embodiment, the period is between 60 seconds and 5 minutes. In another embodiment, the time of exposure to actinic light of the tooth, tissue, skin or wound on which the photoactivatable composition has been applied is dependent on the area of the treatment site. For example, a period between 60 seconds and 5 minutes per $cm^2$ of the area may be treated, so that the total time of exposure of a 10 $cm^2$ area would be between 10 minutes and 50 minutes. In certain embodiments, the time of exposure of actinic light on the treatment site is for a duration sufficient to achieve the desired results. In yet another embodiment, the source of actinic light is in continuous motion over the treated area for the appropriate time of exposure. In yet another embodiment, multiple applications of the photoactivatable composition and actinic light are performed. In some embodiments, the tooth, tissue, skin or wound is exposed to actinic light at least two, three, four, five, six or more times in a given period, such as a day, a week or a month. For example, the treatment site may be exposed to actinic light twice a week, or any suitable amount of time to achieve the desired effect. In some embodiments, a fresh application of the photoactivatable composition is applied before exposure to actinic light.

One key aspect of the photodynamic therapy device of the present invention is that the illuminating element (the source of light) and the photoactivatable composition are in very close proximity (e.g, 0-10 cm), which results in very efficient transmission of light energy to the composition and therefore a rapid and efficient activation of the photoactivatable composition. For example, the illuminating element may be placed within a distance of 2 cm from the photoactivatable composition. The close proximity of the illuminating element to the photoactivatable composition also results in the photodynamic therapy device performing at least as well as standard phototherapy protocol where more powerful light sources are usually used. The photodynamic therapy device requires much smaller quantities of photoactivatable composition to treat the area of interest, as the composition is activated and applied at the same time, directly to the treatment area. Moreover, the composition used in the photodynamic therapy device described herein is non-toxic and thus safer for handling by a user. Also, greater activation of the photodynamic composition may be obtained through the use of a smaller reservoir, where light energy is concentrated, along with the mechanical energy input (e.g., application of the applicator cartridge to the treatment surface).

Example I

A user applies composition from a dual chambered tube to an applicator head having a plurality of fingers and/or bristles extending from the surface of the applicator head. For example, the applicator head 12 from FIGS. 5A-5B, having a plurality of fingers 40, may be used. The dual chambered tube separates an active composition from an oxidizing composition. The compositions are mixed as they exit the dual chambered tube to be placed on the applicator head. The user turns the illuminating member on and applies the applicator head, including the plurality of fingers, on his teeth, with a motion similar to brushing teeth. Light application is applied to the incisors, while more vigorous application is applied to the canines, for about 1 second to 1 minute per tooth, or for a duration necessary to achieve the desired result. The patient then proceeds to rinse his mouth with water to flush away the photoactivatable composition. The procedure may be repeated one or more times until the desired result is achieved.

In another example, the photoactivatable device is used one time daily after brushing, at night. The total application time is approximately 3 minutes. During each use, 0.5 ml of composition is used. After approximately 10 days, the color shift of the teeth will be at least 2 shades of the Vita scale.

Example II

A user applies antibacterial periodontal composition to an applicator head having a plurality of fingers and/or bristles extending from the surface of the applicator head. For example, the applicator head 12 from FIGS. 5A-5B, having a plurality of fingers 40, may be used. The antibacterial periodontal composition is prepared by mixing the following components: an oxidant, healing factors, and photoactivators. The resulting composition is illuminated with actinic light for less than 5 minutes before application to the mouth of a patient. Application of the applicator head to the user's mouth may be similar to the motion used for brushing teeth. In certain embodiments the applicator head is applied directly to at least one of the user's gums and tongue. After application, the composition is left in the mouth for less than 5 minutes. The composition is removed following treatment. The procedure may be repeated one or more times until the desired result is achieved.

Example III

An applicator cartridge containing a wound healing composition is mounted on the illuminating member. The user presses a lid to mix one or more compositions coated on the lid with one or more compositions within the reservoir. For example, the applicator cartridge 10 illustrated in FIG. 1 may be used. The user turns the illuminating member on and applies the applicator head to a wound, for example, on his left arm. Light application is applied to the wound, for about 1 second to 5 minutes, or for a duration necessary to achieve the desired result. The actinic light is concentrated on the treatment site during application. A second application may be made a few minutes later, again for a period of about 1 second to 5 minutes. The patient then wipes the composition from the treatment site and proceeds to cover wound with a sterile gauze. The above procedure may be repeated as many times as necessary to achieve the desired result (e.g., the wound is healed).

Example IV

An applicator cartridge containing a skin condition treatment composition is mounted on the illuminating member. The user presses a lid to mix one or more compositions coated on the lid with one or more compositions within the reservoir. For example, the applicator cartridge 10 illustrated in FIG. 1 may be used. The user turns the illuminating member on and applies the applicator head to a skin condition, such as on a port wine stain located on her left cheek. Light application is applied to the port wine stain, for about 1 second to 10 minutes, or until the skin condition is treated. The actinic light is concentrated on the treatment site during application. The composition is left on the stain for a few minutes, and then wiped away. Subsequent applications are made in the following days, again for necessary periods (e.g., 5 minutes), until the skin condition has paled or disappeared.

Example V

An applicator cartridge containing a skin rejuvenation composition is mounted on the illuminating member. The user presses a lid to mix one or more compositions coated on the lid with one or more compositions within the reservoir. For example, the applicator cartridge 10 illustrated in FIG. 1 may be used. The user turns the illuminating member on and applies the applicator head to the skin, for example to create tighter skin. Light application is applied to the skin, for about 1 second to 10 minutes, or until the skin is rejuvenated. The actinic light is concentrated on the treatment site during application. The composition is left on the skin for a few minutes, and then wiped away. Subsequent applications are made in the following days, again for necessary periods (e.g., 5 minutes), until the skin has approved in appearance and/or becomes tighter.

It is to be understood that while various illustrative embodiments have been described, the foregoing description is merely illustrative and does not limit the scope of the invention. While several examples have been provided in the present disclosure, it should be understood that the disclosed systems, components, and methods may be embodied in many other specific forms without departing from the scope of the present disclosure.

The examples disclosed can be implemented in sub-combinations with one or more other features described herein. A variety of systems and methods may be implemented based on the disclosure and still fall within the scope of the invention. Also, the various features described or illustrated above may be combined or integrated in other systems or certain features may be omitted, or not implemented.

Examples of changes, substitutions, and alterations are ascertainable by one skilled in the art and could be made without departing from the scope of the information disclosed herein. Certain particular aspects, advantages, and modifications are within the scope of the following claims.

The claims hereof are to be understood to include, without limitation, all alternative embodiments and equivalents of the subject matter hereof. Phrases, words and terms employed herein are illustrative and are not limiting. Where permissible by law, all references cited herein are incorporated by reference in their entirety. It will be appreciated that any aspects of the different embodiments disclosed herein may be combined in a range of possible alternative embodiments, and alternative combinations of features, all of which varied combinations of features are to be understood to form a part of the subject matter claimed.

The invention claimed is:

1. A phototherapy device comprising:
an illuminating member comprising an illuminating element and a power source electrically connected thereto; and
a light permeable cartridge comprising an applicator head having a planar surface at a distal end, an absorbent pad placed onto the planar surface of the applicator head, and a reservoir adapted to receive therein a composition, wherein the applicator head comprises one or more pores for passing the composition from the reservoir through the applicator head onto a treatment site, wherein the light permeable cartridge allows passage of actinic light from the illuminating element to the treatment site, wherein the cartridge is detachably connected to the illuminating member, and wherein when the cartridge is connected to the illuminating member, the reservoir is positioned between the applicator head and the illuminating member.

2. The device of claim 1, wherein the device is a handheld device.

3. The device of claim 1, wherein the cartridge comprises a mounting member for mounting the cartridge on the illuminating member.

4. The device of claim 3, wherein the mounting member is threaded.

5. The device of claim 3, wherein the mounting member includes a clip.

6. The device of claim 1, wherein the applicator head comprises a plurality of fingers extending from the distal end of the applicator head.

7. The device of claim 1, wherein the cartridge comprises a removable cover member adapted to cover the applicator head.

8. The device of claim 7, wherein the removable cover member is coated with a composition.

9. The device of claim 8, wherein the composition coating the removable cover member comprises a photoactivator and/or an oxidant.

10. The device of claim 7, wherein the removable cover member is impermeable to light.

11. The device of claim 1, wherein the cartridge is made from a flexible material.

12. The device of claim 1, wherein the cartridge is made from an inert material.

13. The device of claim 1, wherein the distance between the illuminating element and the applicator head is 0-10 cm.

14. The device of claim 1, wherein the illuminating member further comprises a waveguide, the waveguide being connected to the illuminating element.

15. The device of claim 14, wherein the waveguide comprises at least one optical fiber.

16. The device of claim 14, wherein the waveguide comprises at least one light pipe.

17. The device of claim 1, wherein the illuminating element is a light emitting diode (LED).

18. The device of claim 17, wherein the LED is configured to emit an actinic visible light.

19. The device of claim 1, wherein the illuminating element is configured to emit an actinic continuous light.

20. The device of claim 1, wherein the illuminating element is configured to emit an actinic pulsed light.

21. The device of claim 1, wherein the device can be hand mounted or finger mounted.

22. The device of claim 1, wherein the reservoir and/or the cartridge is removable.

23. The device of claim 1, further comprising one or more actuator buttons for controlling the illuminating element and/or for pushing a composition in the reservoir through the one or more pores.

24. The device of claim 1, wherein the cartridge is configured to push through a composition in the reservoir through the pores of the applicator head when a pressure is applied to the cartridge.

25. The device of claim 1, further comprising a composition in the reservoir, said composition comprising a photoactivator and/or an oxidant.

26. The device of claim 1, wherein the composition comprises a xanthene or xanthene derivative.

* * * * *